United States Patent
Bär et al.

(10) Patent No.: US 8,641,974 B2
(45) Date of Patent: Feb. 4, 2014

(54) DEVICE FOR MAGNETIC DETECTION OF INDIVIDUAL PARTICLES IN A MICROFLUID CHANNEL

(75) Inventors: Ludwig Bär, Erlangen (DE); Oliver Hayden, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 245 days.

(21) Appl. No.: 12/734,899

(22) PCT Filed: Nov. 27, 2008

(86) PCT No.: PCT/EP2008/066305
§ 371 (c)(1),
(2), (4) Date: Jun. 1, 2010

(87) PCT Pub. No.: WO2009/068598
PCT Pub. Date: Jun. 4, 2009

(65) Prior Publication Data
US 2010/0273184 A1    Oct. 28, 2010

(30) Foreign Application Priority Data
Nov. 30, 2007  (DE) .......................... 10 2007 057 667

(51) Int. Cl.
*G01N 27/00* (2006.01)
(52) U.S. Cl.
USPC ......... 422/82.02; 422/50; 422/82.01; 422/96; 422/430; 422/68.1; 435/283.1; 435/287.2

(58) Field of Classification Search
USPC .............. 422/50, 82.01, 82.02, 96, 430, 68.1; 435/283.1, 287.2
See application file for complete search history.

(56) References Cited

U.S. PATENT DOCUMENTS

| | | | |
|---|---|---|---|
| 2005/0127916 A1* | 6/2005 | Tondra | 324/324 |
| 2006/0081954 A1 | 4/2006 | Tondra et al. | |
| 2007/0228500 A1* | 10/2007 | Shimazu et al. | 257/417 |

FOREIGN PATENT DOCUMENTS

| | | |
|---|---|---|
| WO | WO 0026669 A1 | 5/2000 |
| WO | WO 0127592 A1 | 4/2001 |
| WO | WO 03054566 A1 | 7/2003 |
| WO | WO 2007092909 A2 | 8/2007 |

OTHER PUBLICATIONS

European Search Report dated Dec. 17, 2010 and issued in corresponding European Patent Application 08 853 611.5.
Jiang Z et al: An integrated microfluidic cell for detection, manipulation, and sorting of single micron-sized magnetic beads Journal of Applied Physics, American Institute of Physics: New York, U.S., vol. 99, No. 8, Apr. 26, 2006, pp. 1-3, XP012084910, ISSN: 0021-8979.
Rife J C et al: Design and performance of GMR sensors for the detection of magnetic microbeads in biosensors Sensors and Actuators A, Elsevier Sequoia S. A., Lausanne, CH, vol. 107, No. 3, Nov. 1, 2003, Nov. 2003, pp. 209-218, XP004469965 ISSN: 0924-4247.

(Continued)

*Primary Examiner* — Melanie Y Brown
(74) *Attorney, Agent, or Firm* — Staas & Halsey LLP

(57) ABSTRACT

A device dynamically detects particles of a fluid. The device can be miniaturized for detecting and selecting magnetized particles, particularly cells.

13 Claims, 3 Drawing Sheets

AA Microfluidic channel
BB Cells

(56) References Cited

OTHER PUBLICATIONS

Mitrelias et al: Biological cell detection using ferromagnetic microbeads Journal of Magnetism and Magnetic Materials, Elsevier Science Publishers, Amsterdam, NL, [Online] vol. 310, No. 2, Mar. 16, 2007, pp. 2862-2864, XP022048775 EVL ISSN: 0304-8853.

Ludwig F et al: Magnetorelaxometry of magnetic nanoparticles with fluxgate magnetometers for the analysis of biological targets Journal of Magnetism and Magnetic Materials, [Online] vol. 293, May 3, 2005, pp. 690-695, XP002520483 ISSN: 0304-8853 Found on the Internet: URL: http://www.sciencedirect.com/> [found on Mar. 19, 2009].

D. Huh, W. Gu, Y. Kamotani, J. B. Grotberg, and S. Takayama, "Microfluidics for flow cytometric analysis of cells and particles", Physiological Measurement 26 (3), R73-R98 (2005).

\* cited by examiner

AA Microfluidic channel
BB Cells

DEVICE FOR MAGNETIC DETECTION OF INDIVIDUAL PARTICLES IN A MICROFLUID CHANNEL

CROSS REFERENCE TO RELATED APPLICATIONS

This application is based on and hereby claims priority to PCT Application No. PCT/EP2008/066305 filed on Nov. 27, 2008 and DE Application No. 10 2007 057 667.8 filed on Nov. 30, 2007, the contents of which are hereby incorporated by reference.

BACKGROUND

The invention relates to a device for detecting particles of a fluid, in particular for magnetically detecting the particles.

By immunofluorescence, marked particles, particularly also cell populations, can be analyzed and separated using a FACS system (FACS: Fluorescence Activated Cell Sorting/flow cytometry) (D. Huh et al., Physiol. Meas. 2005, 26, R73-R98). For this purpose, a cell population is pumped though a capillary tube where individual cells are consecutively checked for their fluorescent properties by an external optical system. Immediately after fluorescence detection, the cells are individually atomized into droplets in a nozzle and the droplets with marked cells are electrically charged. By deflection of the charged droplets in an electric field, the marked cells can be separated from a large cell population. FACS sorters here employ multiple markers and operate at speeds of ~$10^5$ cells/min. This method constitutes the industry standard. The disadvantage of FACS lies in the high procurement and maintenance costs, and in the complexity of the system which requires trained personnel to operate it.

In addition to FACS separation, systems based on immunomagnetic principles are described in the literature, the emphasis here being mainly on the detection of marked cells and less on separation. Macroscopic dipole and quadrupole separators are used, as well as SQUIDS[1] (Superconducting Quantum Interference Device). The disadvantages of these magnetic approaches are their impracticability (no miniaturization possible) and the high costs. Dipole and quadrupole systems, like FACS sorters, are complex and expensive instruments which, because of their size, exhibit only low marked cell recovery rates. SQUIDS must be cooled to below 100 K to be operational. In addition, the cooling necessitates a complex detector design which undermines the high sensitivity of SQUIDS.

In modern cell separation systems, MACS (Magnetic Activated Cell Sorting) is used. Here paramagnetic nanoparticles coated with monoclonal antibodies are mixed with a cell suspension. The antibodies bind to the specific antigen on the cell surface. If the cell suspension passes through a powerful magnetic field in a column, the cell/nanoparticle complexes remain in the column, while the free cells momentarily flow through (negative selection). If the column is removed from the magnetic field, the cell/nanoparticle complexes can be recovered (positive selection). Cells attaching to microbeads are viable and the bead/antibody complex can be removed from the cell surface. MACS is completely FACS-compatible. Following magnetic separation (100× accumulation of up to $10^9$ cells in 15 min)[2], flow cytometry analysis with fluorescence marking can take place. The disadvantage of this process is the need for double marking (magnetic and fluorescence) in order to perform cost-effective analysis/refined separation of the cells.

SUMMARY

One possible object is therefore to overcome the disadvantages of the related art and to create an inexpensive and accurate device and a method for detecting magnetically labeled particles, particularly cells.

The inventors propose a device for dynamically detecting and selecting magnetically labeled particles, comprising a microfluidic channel and, disposed around same, a Wheatstone bridge circuit with at least one magnetoresistive element, the microfluidic channel being disposed in the bridge circuit such that the magnetically labeled particles flowing through the microfluidic channel measurably influence the balance of the bridge circuit.

The inventors also propose a method for dynamically detecting and selecting magnetically labeled particles, wherein magnetically labeled particles flow through a microfluidic channel and, due to the magnetic stray field generated by them, influence at least one magnetoresistive resistor of the Wheatstone bridge disposed around the microfluidic channel so as to produce a measurable deflection of the bridge.

Advantageously, at least two types of magnetically labeled particles are used, namely permanently magnetized particles whose dipole moment remains even after removal of an external magnetic field required for the magnetization, and temporarily magnetically labeled particles, e.g. so-called superparamagnetic particles, particularly also nanoparticles. These particles are temporarily magnetized by an external magnetic field upstream of the device and the magnetization decays with a characteristic decay time as a function of the superparamagnetic particle. The difference in the decay time enables the dynamic detection and selection described here to be carried out.

The last mentioned magnetically marked particles are particularly preferred for the dynamic detection and selection described here.

Ferromagnetic particles, on the other hand, are not preferred, as there is a risk of them forming clumps and, in this approach, interfering with the sensor or blocking the microfluidic channel.

Stray field means that the field generated by the magnetically labeled particles has been induced by an external field.

Superparamagnetic particles are produced by magnetically polarizing them in the external field. If the field is removed, with a certain decay time no dipole remains.

The dynamic measurement is performed using a microfluidic channel. The microfluidic channel is matched to the size of the examined particles, particularly cells, in order to enable individual detection with high recovery rate. According to a preferred embodiment, the microfluidic channel is formed using a micromechanical method, e.g. by etching of a silicon wafer. The microfluidic channel is preferably matched such that each particle or each cell flows individually through the microfluidic channel, i.e. there is no room in the channel for a plurality of adjacent particles. For example, the microfluidic channel can also be produced by a forming technique such that it is made e.g. by pouring a silicone over a silicon punch. The microfluidic channel is preferably made of transparent material.

In addition to dynamic detection and selection, another optical, electrical, magnetic and/or other detection method can also be used to analyze the fluid in the microchannel.

The detection possibilities:
a) Optical:
All the cells in a microfluidic channel are detected by microscopy, absorption or fluorescence measurement and the fraction of marked cells is calculated by comparison measurement using a magnetoresistive device.

b) Electrical:

Similarly to optical determination, the flow rate of individual cells in the microfluidic channel is counted by impedance spectroscopy, capacitive, resistive or dielectrophoretic measurement methods and the fraction of magnetically marked cells is again calculated by differential measurement with the registered number of marked cells by measurement using a magnetoresistive detector.

c) Magnetic (1 type of magnetic nanoparticle):

Each cell flowing through the microfluidic channel—matched to the cell dimension—is forced into the aqueous solution in the region of the magnetoresistive sensor because of the cell volume and therefore fewer unbound magnetic nanoparticles will be present. This temporary nanoparticle depletion results in a reduced measurement signal and permits the detection of unmarked cells. In the case of a marked cell, a large measurement signal is detected, as the magnetic nanoparticles accumulate on the cell surface or inside the cell.

d) Magnetorelaxometry:

The decay of the magnetic moment of nanoparticles is determined by the size of the particle itself and by the binding to other particles or substrates. Valuable additional information can be obtained by determining the different relaxation times by time-resolved measurements with the magnetoresistive sensor. For example, bound and unbound cells can be differentiated. It is conceivable to provide various cell types or cells with different antigen bonds and bind respective nanoparticles with different size sorting. Different sized cells as ligands to the same kind of magnetic nanoparticles can also be differentiated in this way.

The proposed solution is based on the use of magnetoresistive components which are incorporated in the microfluidic channels. Unlike in all immunomagnetic approaches hitherto, cell detection takes place dynamically during the flow of cells through a microfluidic channel. The setup is schematically illustrated in the accompanying drawings. A Wheatstone bridge arrangement of generally 4 magnetoresistive resistors is disposed such that two resistors are mounted below a microfluidic channel and two resistors remain outside the microfluidic region in order to achieve maximum unbalancing of the bridge by magnetically marked cells. However, the arrangement of the 4 elements is variable and, depending on the arrangement, the signal sensitivity or local resolution of the device and of the method can be optimized.

Moreover, there do not necessarily have to be 4 magnetoresistive elements in the bridge circuit. It is equally possible for 2 magnetoresistive elements to be combined with two conventional resistors in the bridge. Or any other combination, as long as at least one magnetoresistive element is present in the bridge circuit.

The magnetoresistive elements can be both conventional magnetoresistive elements, as described e.g. in DE 102 02 287, or organic magnetoresistive elements as disclosed, for example, in DE 10 2006 019 482.

Analysis and separation of particles, e.g. heterogeneous cell populations, on the basis of cellular features is accessible by magnetoresistive measurements. For the separation of the heterogeneous cell populations, immunomagnetic markers (nanoparticles bound to a receptor or ligand) are used. The marked cells are magnetized in an external magnetic field, thereby generating an additional magnetic stray field which can be detected by a magnetoresistive component. Through the use of magnetorelaxometry (decay of the stray field over time), unbound and different bound magnetic nanoparticles can be differentiated from one another. No other fluorescence markings or similar are necessary for the separation or analysis of the cell population.

The marked cells are detected by a magnetoresistive component, whereas the unmarked cells can be optically, electrically or magnetoresistively detected.

The proposed device and method have the potential to replace fluorescence measurement in conventional FACS analysis. For this type of fluorescence-based cell detection mentioned in the introduction, the cells are introduced into a small capillary tube. Fluorescence detection takes places discretely on individual cells. The individual cells are atomized into small droplets and electrically charged as a function of fluorescence detection. The charged droplets are deflected in a collector and collected in a vessel.

The GMR sensor is here inserted upstream of the atomizer. Measurements into the MHz range can be performed with this setup. The advantage of this design is its massive potential for miniaturization and parallelization. In addition to separation using an atomizer, analysis of the cell population can also be performed.

In hitherto known applications of GMR sensing in biology and medicine (DNA sensor), immobilized, magnetically marked material is detected, a statistical selection method being used. For the dynamic measurement of individual analytes, high-frequency interrogation of the sensor status is advantageous. This is implemented e.g. by field scanning of the sensor in the relevant region of the characteristic at frequencies typically significantly higher than 1 kHz. A deviation in the sensor amplitude or a step-change in the sensor sensitivity (differentiated signal) are e.g. an indication of event detection.

This selection method additionally allows electronic lock-in filtering to be used for conditioning of the wanted signal, thereby enabling event detection sensitivity to be significantly increased.

The magnetoresistive sensor is advantageously implemented by disposing at least one magnetoresistive element in the form of a Wheatstone bridge. For dynamic detection of magnetic particles, the elements of the bridge are spaced at least the particle size apart. The bridge then has an effective extent of four particle diameters. This means that detecting closely consecutive particles becomes a problem. Assuming that the fluidic channel can be precisely microfabricated and positioned on a carrier chip with a high degree of accuracy, the geometry of the bridge circuit can be modified such that two diagonal elements of the Wheatstone geometry lie inside and the two other diagonal elements outside the microfluidic cell, thereby doubling the local resolution for particle detection.

In another exemplary embodiment, three bridge elements are placed outside the detection region. Although this halves the signal sensitivity of the sensor, the local resolution is quadrupled.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
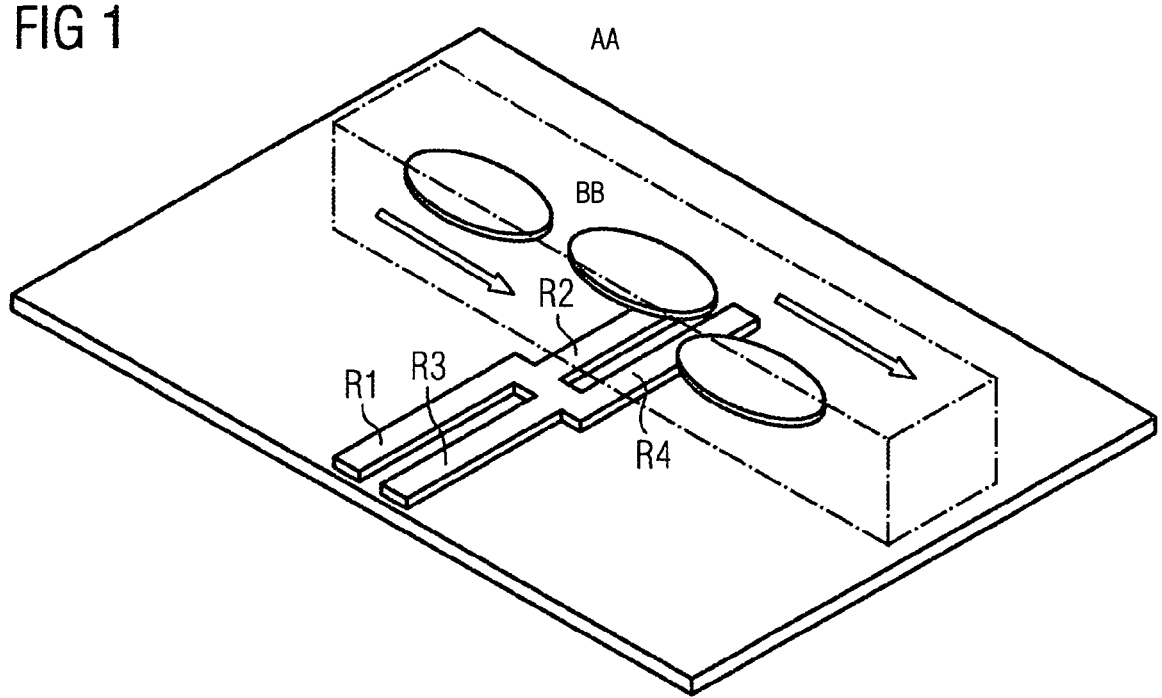
FIG. 1 shows the circuit diagram of an embodiment of the proposed device.

Reference will now be made in detail to the preferred embodiments of the present invention, examples of which are illustrated in the accompanying drawings, wherein like reference numerals refer to like elements throughout.

FIG. 1 shows a typical setup for a geometric arrangement of the bridge in which 2 bridge elements, i.e. two magnetoresistive resistors R1 and R3, for example, are disposed outside the microfluidic channel 1, and 2 bridge elements, again either electrical or magnetoresistive resistors R2 and R4, are disposed below the microfluidic channel, i.e. inside the so-called detection region of the microfluidic channel. At least one resistor is a magnetoresistive resistor. Individual cells 2 are to be detected in the fluidic channel 1. The arrows indicate the direction of fluid flow.

Figure 2:
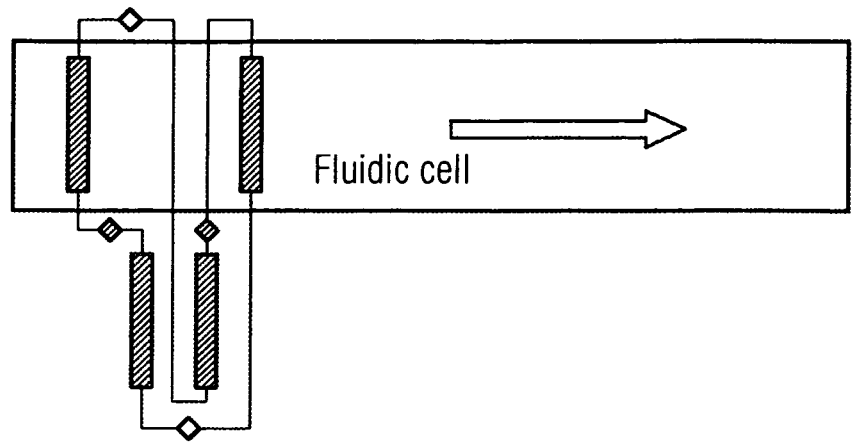
FIG. 2 shows the magnetic relaxation of magnetic nanoparticles

FIG. 2 shows a variant of the Wheatstone bridge arrangement. Again visible are the fluidic channel 1 and 4 resistors R1 to R4 disposed in a Wheatstone bridge circuit.

Figure 3:
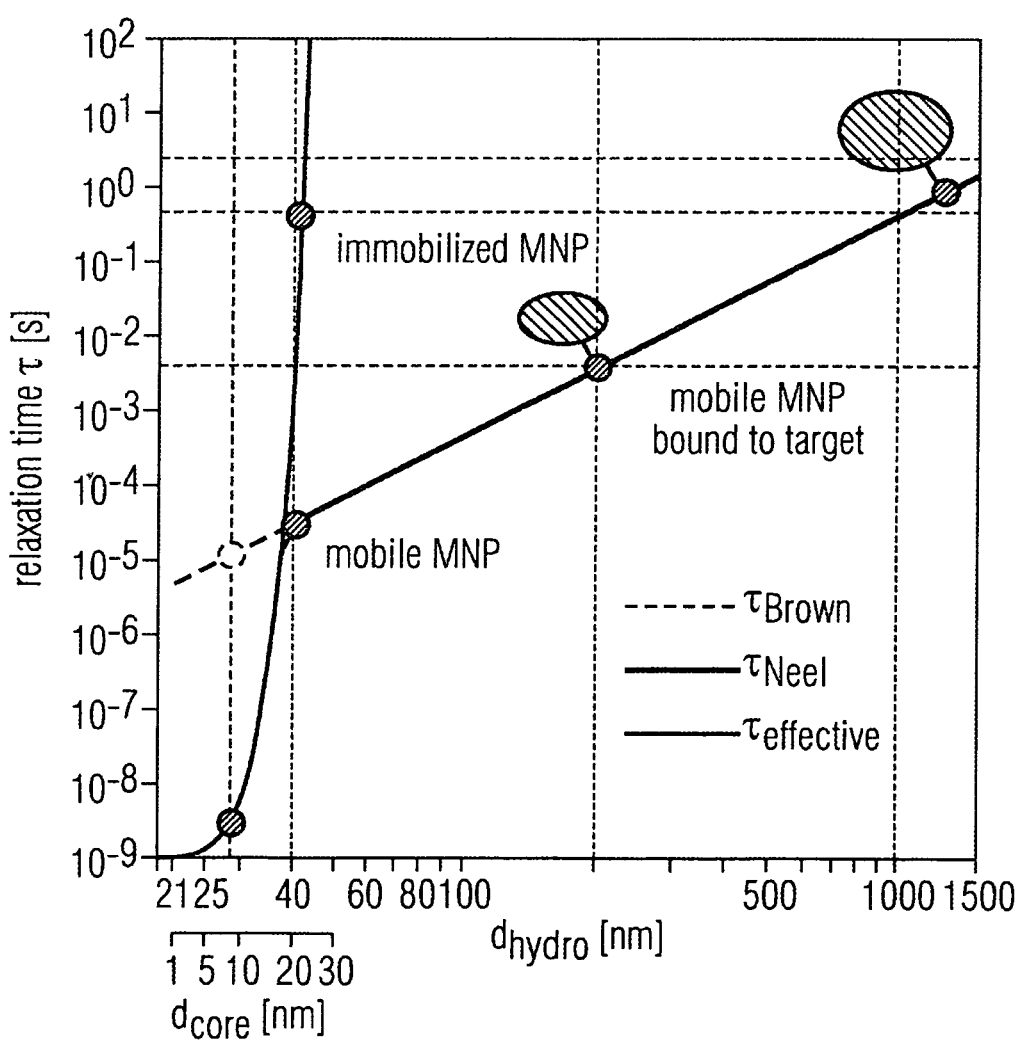
FIGS. 3 and 4 show an example of high-frequency interrogation of the sensor status of the measurement.

FIG. 3 shows by way of example how the magnetic relaxation of magnetic nanoparticles is measured. This figure shows an extract from the publication of F. Ludwig, E. Heim, S. Mauselein, D. Eberbeck and M. Schilling: "Magnetorelaxometry of magnetic nanoparticles with fluxgate magnetometers for the analysis of biological targets" J Magnet Magn. Mat. 2005; 293(1):690-695.

Figure 4:
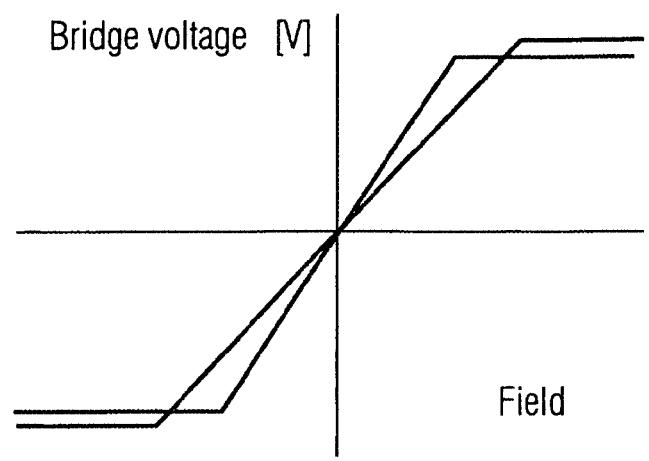

FIG. 4 shows a diagram of the signal amplitude and

Figure 5:
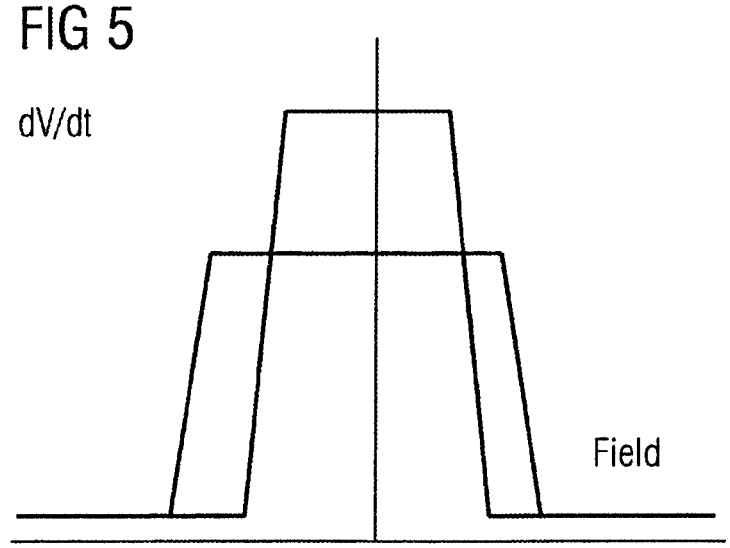
FIG. 5 shows a diagram of the sensor sensitivity.

FIG. 5 shows a diagram of the sensor sensitivity.

Fluorophores can be metabolized or fade in long-term tests. Magnetic nanoparticles are bio/chemically resistant and optically indifferent.

The reaction kinetics can therefore be continuously tracked e.g. in a miniaturized system.

The proposed device and method are suitable, among other things, for long-term studies. The chemically stable nanoparticles can be added to a cell experiment over long periods of time.

For example, they can be used to continuously study the expression of surface proteins. Other possible applications include cell adhesion tests, toxicity tests and more besides.

With the proposals, a dynamic and readily miniaturizable method for detecting and selecting magnetized particles, particularly cells, is demonstrated for the first time.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

The invention claimed is:

1. A device for dynamic detection and selection of magnetically labeled cells, comprising:
    a microfluidic channel; and
    a Wheatstone bridge circuit with at least one magnetoresistive element, the Wheatstone bridge circuit being provided in a vicinity of the microfluidic channel such that the microfluidic channel runs along the Wheatstone bridge circuit and such that magnetically labeled cells flowing through the microfluidic channel measurably influence a balance of the Wheatstone bridge circuit wherein the device has at least two bridge elements disposed outside a detection region of the microfluidic channel such that:
    two bridge elements are disposed outside the detection region of the microfluidic channel and two bridge elements are disposed inside the detection region of the microfluidic channel,
    diagonal elements of the Wheatstone bridge circuit are formed by two bridge elements disposed outside the detection region of the microfluidic channel,
    the bridge elements of the Wheatstone bridge circuit are spaced apart by at least the size of the cells, and
    a distance between the two bridge elements disposed inside the detection region of the microfluidic channel is greater than a distance between the two bridge element disposed outside the detection region of the microfluidic channel,
    wherein the device comprises means for obtaining additional information about the magnetically labeled particles by determining different magnetization relaxation times by time-resolved measurements using a magnetorresistive sensor.

2. The device as claimed in claim 1, wherein the magnetically labeled cells are superparamagnetic cells.

3. The device as claimed in claim 1, wherein the microfluidic channel width is matched to a size of the cells such that the cells pass individually through the channel.

4. The device as claimed in claim 1, wherein the microfluidic channel is composed of a transparent material.

5. The device as claimed in claim 1, wherein the bridge elements are disposed such that the Wheatstone bridge has an effective extent of four cell diameters.

6. A device for dynamic detection and selection of magnetically labeled cells, comprising:
    a microfluidic channel; and
    a Wheatstone bridge circuit with at least one magnetoresistive element, the Wheatstone bridge circuit being provided in a vicinity of the microfluidic channel such that the microfluidic channel runs along the Wheatstone bridge circuit and such that magnetically labeled particles flowing through the microfluidic channel measurably influence a balance of the Wheatstone bridge circuit wherein
    the device has at least two bridge elements disposed outside a detection region of the microfluidic channel such that:
    the device has two bridge elements disposed outside the detection region of the microfluidic channel and two bridge elements disposed inside the detection region of the microfluidic channel,
    diagonal elements of the Wheatstone bridge circuit are formed by two bridge elements disposed outside the detection region of the microfluidic channel,
    the bridge elements of the Wheatstone bridge circuit are spaced apart by at least the size of the cells, and
    a distance between the two bridge elements disposed inside the detection region of the microfluidic channel is greater than a distance between the two bridge element disposed outside the detection region of the microfluidic channel.

7. The device as claimed in claim 6, wherein the two bridge elements disposed inside the detection region are disposed below the microfluidic channel, and the magnetically labeled cells flow through the microfluidic channel in a direction perpendicular to a longitudinal axis of the two bridge elements disposed inside the detection region.

8. A method for dynamically detecting and selecting magnetically labeled cells in a device for dynamic detection and selection of the magnetically labeled cells, comprising:
- allowing magnetically labeled cells to flow through a microfluidic channel and generate a magnetic stray field; and
- influencing at least one magnetoresistive resistor of a Wheatstone bridge circuit disposed in a vicinity of the microfluidic channel, the magnetoresistive resistor being influenced by the magnetic stray field so as to produce a measurable deflection of the Wheatstone bridge circuit to thereby detect and select the magnetically labeled cells,
- wherein the microfluidic channel runs along the Wheatstone bridge circuit and the magnetically labeled cells flowing through the microfluidic channel measurably influence a balance of the Wheatstone bridge circuit, wherein the device has at least two bridge elements disposed outside a detection region of the microfluidic channel such that:
- two bridge elements are disposed outside the detection region of the microfluidic channel and two bridge elements are disposed inside the detection region of the microfluidic channel,
- diagonal elements of the Wheatstone bridge circuit are formed by two bridge elements disposed outside the detection region of the microfluidic channel,
- the bridge elements of the Wheatstone bridge circuit are spaced apart by at least the size of the cells, and
- a distance between the two bridge elements disposed inside the detection region of the microfluidic channel is greater than a distance between the two bridge element disposed outside the detection region of the microfluidic channel,
- wherein the device comprises means for obtaining additional information about the magnetically labeled particles by determining different magnetization relaxation times by time-resolved measurements using a magnetoresistive sensor.

9. The method as claimed in claim 8, wherein the magnetically labeled cells are superparamagnetic cells.

10. The method as claimed in claim 8, further comprising analyzing the magnetically labeled cells flowing through the microfluidic channel using an optical, electrical or magnetic analysis method.

11. The method as claimed in claim 8, further comprising performing a Fluorescence Activated Cell Sorting (FACS) analysis on the magnetically labeled cells.

12. The method as claimed in claim 8, wherein
- the magnetically labeled cells have surface proteins, and
- the method further comprises studying an expression of the surface proteins based on the influence of the magnetoresistive resistor of the Wheatstone bridge circuit.

13. The method as claimed in claim 8, further comprising performing a cell adhesion and/or toxicity test based on the influence of the magnetoresistive resistor of the Wheatstone bridge circuit.

* * * * *